United States Patent
Merideth

Patent Number: 6,164,277
Date of Patent: Dec. 26, 2000

[54] AUDIO GUIDED INTUBATION STYLET

[76] Inventor: John H. Merideth, 3685 Watertown Rd., Orono, Minn. 55359

[21] Appl. No.: 09/206,891

[22] Filed: Dec. 8, 1998

[51] Int. Cl.[7] .................................................. A61M 16/00
[52] U.S. Cl. ..................... 128/207.14; 128/898; 606/108
[58] Field of Search .......................... 128/200.24, 204.18, 128/207.14–107.17, 207.29, 898; 606/108

[56] References Cited

U.S. PATENT DOCUMENTS

| | | |
|---|---|---|
| Re. 31,377 | 9/1983 | Mylrea et al. . |
| 3,925,616 | 12/1975 | Sondhi . |
| 4,082,088 | 4/1978 | Franetzki et al. . |
| 4,244,362 | 1/1981 | Anderson . |
| 4,248,241 | 2/1981 | Tacchi . |
| 4,366,821 | 1/1983 | Wittmaier et al. . |
| 4,607,643 | 8/1986 | Bell et al. . |
| 4,633,864 | 1/1987 | Walsh . |
| 4,669,463 | 6/1987 | Mcconnell ........................ 128/207.14 |
| 4,917,107 | 4/1990 | Bell et al. . |
| 4,951,678 | 8/1990 | Joseph et al. . |
| 5,000,175 | 3/1991 | Pue ..................... 128/207.14 |
| 5,056,514 | 10/1991 | DuPont . |
| 5,203,320 | 4/1993 | Augustine . |
| 5,257,636 | 11/1993 | White ................. 128/207.14 |
| 5,259,377 | 11/1993 | Schroeder ........................ 128/207.14 |
| 5,400,797 | 3/1995 | Ethridge . |
| 5,445,144 | 8/1995 | Wodicka et al. . |
| 5,560,351 | 10/1996 | Gravenstein et al. . |
| 5,562,078 | 10/1996 | Dzwonkiewicz . |
| 5,620,004 | 4/1997 | Johansen . |
| 5,906,204 | 5/1999 | Beran et al. ........................ 128/207.14 |
| B1 5,083,561 | 5/1993 | Russo ................. 128/207.14 |

OTHER PUBLICATIONS

"Intubation Imaging System for Difficult Airways", *Product Brochure:Nanoscope*, Nanoptics, Inc., Printed Sep. 1997, 4 pages.

"Flexguide Intubating Fiberscope", *Product Brochure: Scientific Sales International, Inc.*, 1 page, (1097).

"Flexguide—An Innovation in Endotracheal Intubation", *Product Brochure: Scientific Sales, Int., Inc.*, 1 page.

(List continued on next page.)

*Primary Examiner*—Glenn K. Dawson
*Attorney, Agent, or Firm*—Schwegman, Lundberg, Woessner & Kluth, P.A.

[57] ABSTRACT

A intubation stylet having a cylindrical guide member is disclosed wherein the guide member has a proximal end, a distal end, and an intermediate section therebetween. The distal end may include a microphone operatively coupled to a sound processing device having a speaker or earphone. The stylet may be passed through an endotracheal tube and into the mouth or nose of a breathing patient. As the distal end is passed into the mouth, the microphone detects audible sounds produced by air movement within the upper airway and generates a raw sound signal based on the audible sounds. The sound processing device generates an amplified sound output signal based on the raw signal and transmits the amplified signal through a speaker. The amplified sounds may then be used as audio cues to assist in guiding the stylet through the larynx and into the trachea. The endotracheal tube may be advanced over the stylet guide member after which the stylet may be removed. In one embodiment, the guide member includes a channel for delivering medicinal substances such as oxygen or anesthetic. The guide member may also include an angulation wire for angulating the distal end relative to the intermediate section to assist in positioning the distal end.

6 Claims, 3 Drawing Sheets

OTHER PUBLICATIONS

"Lifesound Heart/Breath Sound Monitoring System: LS–1030/LS–1040 Transmitter; LS–1100 Pocket Receiver", *Product Brochure: Novasonics,* 2 pages.

"Port–O–Scope III, The Ultimate Fiber Optic Flexible Scope", *Product Brochure: North American Medical Products, Inc. (NAMP)*, 1 page.

"Practice Guidelines for Management of the Difficult Airway, A Report by the American Society of Anesthesiologist Task Force on Management of the Difficult Airway", *Anesthesiology, 78* (3), 597–602, (Mar., 1993).

"The Welch Allyn FL–100 Flexible Intubating Fiberscope", *Product Brochure: Welch Allyn,* Printed in USA, SM 2903, 2 pages.

"Tracheal Intubation Fiberscope Olympus LF–2", *Product Brochure: Olympus,* Printed in Japan F452E–0897B, 2 pages.

"Tracheal Intubation Fiberscope Olympus LF–P" *Product Brochure; Olympus,* Printed in Japan F456E–0994B, 2 pages.

AUDIO GUIDED INTUBATION STYLET

TECHNICAL FIELD

This invention relates to devices for inserting and guiding a tube within a body and, more particularly, to a device and method for correctly positioning an endotracheal tube based on audio cues produced by air movement in a breathing patient.

BACKGROUND OF THE INVENTION

In both elective surgery and emergency medical situations, it is often necessary for medical personnel to secure the airway of the patient through a procedure known as endotracheal intubation. Intubation requires the intubator to insert a tube, either through the mouth or nose, into the trachea of the patient. The tube permits active monitoring and proactive control of the patient's breathing and additionally permits the direct administration of anesthesia or other drugs.

Potential damage to the vocal cords and the danger of esophageal placement (rather than tracheal placement) of the tube dictate that intubation be performed by a skilled professional. However, even an experienced intubator occasionally encounters a patient who has what is commonly referred to as a "difficult" airway.

Patients whose tracheas are difficult to intubate have been well known in the anesthesia community for decades. Intubating difficulties are especially prevalent among those who have: problems with obesity or have short, thick necks or short mandibles; cervical arthritis, temporomandibular joint problems, or previous cervical fusions; fractures of the mandible, maxilla, or cervical spine; tumors or abscesses in the mouth, pharynx or neck; suffered trauma to the face or neck; and those having congenital syndromes.

The American Society of Anesthesiologists has studied respiratory injuries suffered by patients with difficult airways. This study determined that the occurrence of injuries related to difficult intubation is not improving. In the 1970s, for example, such injuries accounted for 5% of malpractice claims that resulted in death or brain damage. In the 1990s, that figure has increased to 12%.

Current devices used for intubating a difficult airway vary depending on the particular situation. For example, in an unhurried elective situation (as before routine surgery), a patient that requires intubation is usually approached with one of several types of fiberoptic scopes. Fiberoptic scopes are popular for elective procedures largely due to their safety record. Since the procedure is elective and not an emergency, an unhurried, careful approach to intubation is possible. Furthermore, failure of fiberoptic intubation typically does not harm the patient.

Unfortunately, fiberoptic scopes are ineffective under certain circumstances. In particular, fiberoptic failure rates are high where there is distortion of the anatomy. For example, fiberoptic failure may occur in the presence of a tumor or abscess or where there is a greatly increased amount of soft tissue present in the upper airway, as is common with morbid obesity. Furthermore, due to their reliance on optics, fiberoptic scopes are difficult to use when blood or excess secretions are present in the airway. In addition to these drawbacks, fiberoptic scopes are generally perceived to be expensive and relatively fragile.

When fiberoptic techniques fail, the alternatives are much more painful and traumatic for the patient and more difficult for the intubator. One option is the insertion of a retrograde wire. This technique involves piercing the larynx just below the vocal cords with a hollow needle and threading a wire upwardly between the vocal cords and into the mouth. An intubation tube may be slid over the wire and into place. Alternatively, a fiberoptic scope having a wire receiving guide may be placed over the wire. Regardless, retrograde wire techniques involve trauma to the larynx that may cause airway bleeding or hematoma. In addition, finding the larynx and placing the wire may be difficult in an obese patient. Furthermore, even if the wire is properly placed, there is a very short distance between the vocal cords and the exit of the wire from the larynx (i.e., the wire will exit the larynx through the neck immediately below the vocal cords). Thus, whatever device is threaded over the wire may easily become dislodged from the glottis when the wire is removed.

Intubators sometimes utilize a lighted stylet having a light source visible outside the neck of the patient. Lighted stylet techniques, however, have the disadvantage of working best in a dark environment. Additionally, they do not work well in patients with thick necks.

Another option is to proceed with the induction of anesthesia and attempt direct laryngoscopy. Direct laryngoscopy involves anesthetizing the patient and inserting a rigid laryngoscope into the mouth to examine the larynx. Unfortunately, such a procedure involves substantial risks. Apnea from the induction agent and paralysis from muscle relaxants can be life-threatening. With even the shortest acting paralytic (succinylcholine), 8–10 minutes is required to reestablish spontaneous ventilation.

Yet another option is to use a laryngeal mask airway (LMA). An LMA is a tube-like device with a oval cup at the distal end designed to form a low pressure seal between the LMA tube and the glottis without insertion into the larynx. Unfortunately, LMAs and other supraglottic devices (e.g., combitude), while appropriate for some types of surgery, are contraindicated in patients who are at risk for regurgitation or esophageal reflux since these devices do not protect the airway from stomach contents.

In addition to elective surgery, difficult intubations are also prevalent in the emergency room (ER). Emergency intubations are generally much more challenging for various reasons. For instance, because blood and excessive secretions in the mouth and/or airway are common, fiberoptic techniques are used less frequently in the ER. Additionally, patients typically are not as cooperative as those undergoing elective procedures. Furthermore, there is often concern about cervical spine injuries that make movement of the neck potentially injurious.

As discussed with respect to elective procedures, direct laryngoscopy with or without drugs is available in the ER. Unfortunately, this procedure poses risk of injury to patients who have suffered cervical spine damage even if manual cervical stabilization is first administered. Direct laryngoscopy with induction agents or paralytics may furthermore cause loss of patency of the airway and aspiration of the stomach contents.

Another option in the ER involves blind nasal techniques. While advantageous in some circumstances, such techniques are potentially dangerous where basilar skull fracture is present. Furthermore, these techniques are known to have a high failure rate.

Some practitioners recommend that the intubator place an ear near the proximal end of the endotracheal tube as it approaches the glottis. Breathing sounds may then be used to indicate the tube position relative to the glottis. Such a technique has drawbacks though. First, coughing by the patient may propel blood and mucus through the tube into the operator's ear or face. Second, the intubator is poorly oriented to observe other aspects of the procedure such as head and neck position, patient response to maneuvers, and vital sign monitors such as pulse oximetry and EKG. Finally, depending on the patient's injuries and the ambient noise in the room, the intubator may be unable to detect any sounds. For these reasons, listening devices for use with endotracheal tubes have been described generally for use after tube insertion for the monitoring of vital signs and sounds.

Other methods are known that provide an external energy source and attempt to locate the trachea based on reflected energy readings. While effective in most circumstances, these devices are complex, requiring an energy source and wave form energy transmitter. As such, these devices are bulky and relatively expensive and are not widely used.

Thus, there are unresolved issues with current devices used for intubating difficult airways in spontaneously breathing patients. Particularly, current devices are expensive and are difficult to use in the presence of anatomical abnormalities (e.g., soft tissues mass, abscess) or blood or secretions in the airway. What is needed is a simple intubating device that is safe to use, inexpensive, and effective in a broad range of circumstances.

SUMMARY OF THE INVENTION

In its broadest form, the present invention is directed to an apparatus for insertion into a patient wherein the patient has a naturally occurring energy source. The apparatus may comprise: a guide portion having a proximal end and a distal end; a first device for determining the location of the distal end relative to the naturally occurring energy source and generating a raw signal based thereon; and a second device for receiving and processing the raw signal to provide assistance in guiding the distal end of the guide portion within the patient.

In a preferred form, the device incorporates a guide portion having a proximal end, a distal end, and an intermediate section therebetween. In a first preferred form, the guide portion is part of an intubation stylet used for inserting an endotracheal tube into the airway of a breathing patient. In a second preferred form, the guide portion comprises an endotracheal tube.

The intubation stylet comprises: a guide portion having a proximal end, a distal end, and an intermediate section therebetween; a transducer for detecting air movement within the airway and generating a raw signal based thereon wherein the transducer is located at the distal end of the guide portion; and a signal processing device coupled to the transducer for receiving and processing the raw signal. The processing device may provide an amplified output signal based on the raw signal. The amplified output signal indicates the position of the distal end of the guide member within the airway.

The stylet may additionally include a control handle connected to the proximal end. The control handle may be connected to an angulation wire passing through the guide member between the distal end and the proximal end. The angulation wire may be operatively coupled to the control handle such that manipulation of the handle results in angulation of the distal end relative to the intermediate section.

The guide member may also include one or more channels extending from the proximal end to the distal end. In one embodiment, the channel may be used to deliver an anesthetic drug, oxygen, or jet ventilation. The guide member may additionally include measuring indicia to indicate the approximate location of the distal end within the patient.

A method for intubating a breathing patient is also herein disclosed. The method comprises inserting an endotracheal tube over an intubating stylet guide member wherein the guide member has a distal end; inserting the distal end into the airway of the patient wherein the distal end includes a microphone; detecting audible sounds at the microphone generated by air passing through the air way; generating a raw electronic signal based on the audible sounds; receiving and processing the raw signal; producing an output signal based on the raw signal; and transmitting the output signal through a sound output device.

The method may additionally include the steps of amplifying the output signal and using the output signal as an audio cue to assist in positioning the distal end. Positioning of the distal end can be achieved by manipulation of an angulation wire within the guide member. In one embodiment, various medicinal fluids may also be delivered through the stylet.

When the stylet has been accurately positioned, the endotracheal tube may be properly positioned and the stylet removed leaving the endotracheal tube in place.

The use of AGIS provides another non-invasive technique having safety characteristics similar to that of fiberoptics. By taking advantage of the auditory characteristics of air movement through the upper airway of a breathing patient rather than the visual appearance of the glottis, AGIS will work in some situations where fiberoptic techniques fail (e.g., in the presence of blood, vomitus or secretions in the airway). Furthermore, it needs no external energy (e.g., light or sound) source. Accordingly, the sound processing device may be a lightweight, portable unit that is convenient to carry. While the AGIS can be used as a backup device to fiberoptics, it may also be chosen as the instrument of choice in the OR, ER, or ICU. As it requires less expertise than fiberoptic techniques, it may also be appropriate for use by field paramedics, an advantage not realized with fiberoptics. Finally, as compared to fiberoptic scopes, AGIS is less expensive, potentially more durable, and less bulky as no light source or heavy electronic equipment is required.

These and other embodiments, aspects, advantages, and features of the present invention will be set forth in part of the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

The invention described herein will be further characterized with reference to the drawings, wherein.

DETAILED DESCRIPTION OF THE PREFERRED EMBODIMENTS

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1:
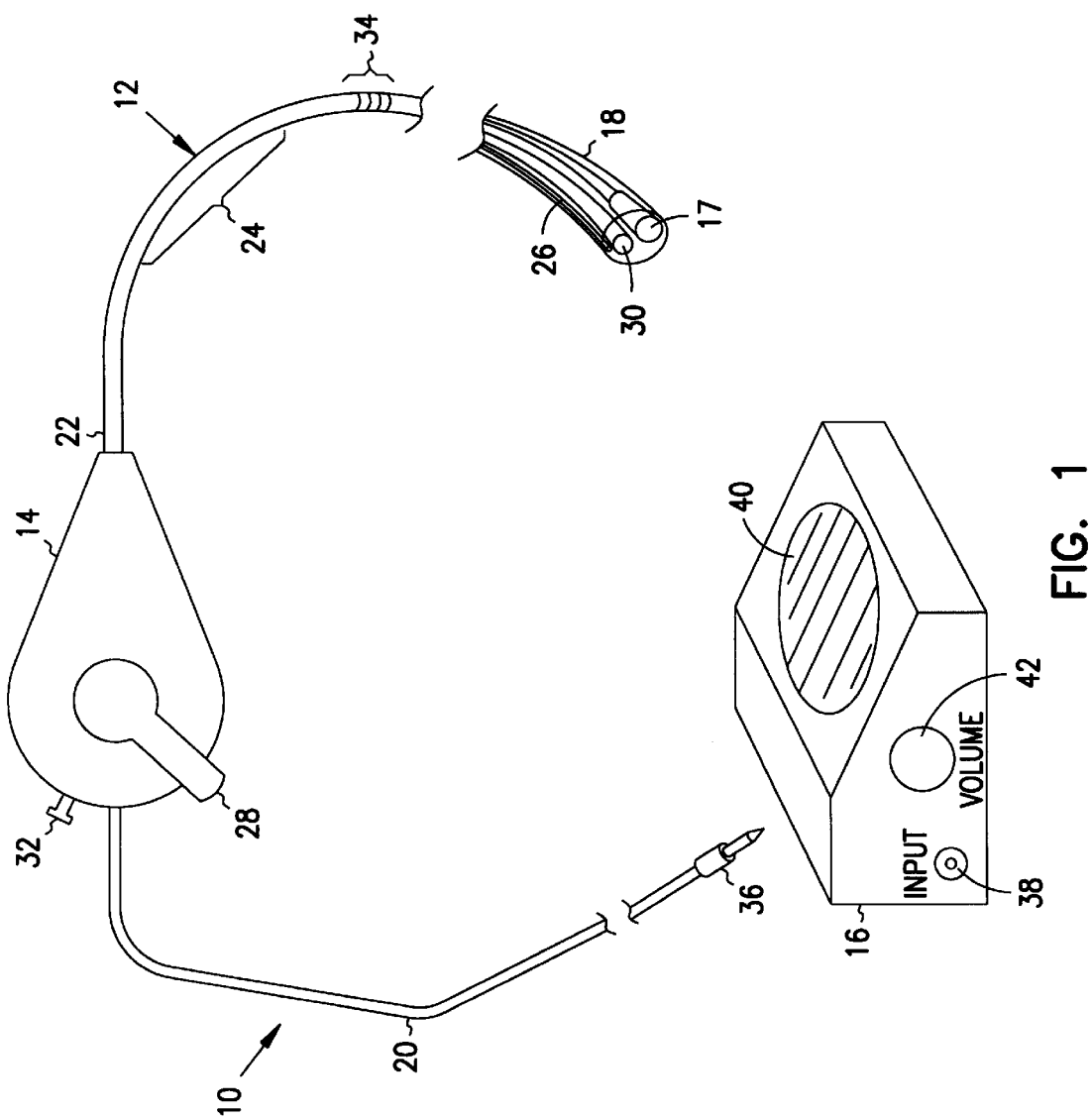
FIG. 1 is a perspective view of an audio guided intubation stylet according to the present invention.
Figure 2:
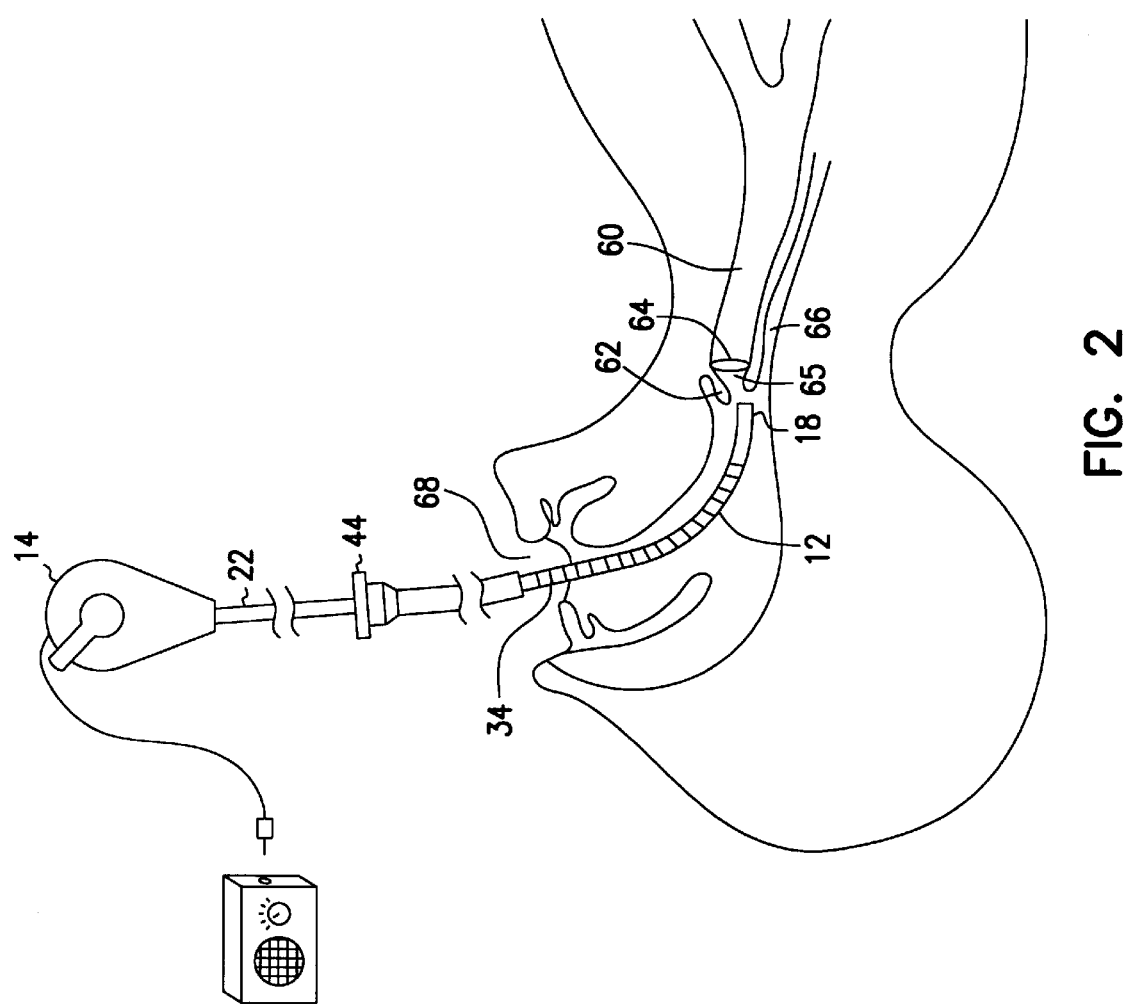
FIG. 2 is a side view of the audio guided intubation stylet of FIG. 1 as used to intubate a patient.

Referring generally to FIG. 1, a first preferred embodiment of an audio guided intubation stylet (hereinafter AGIS) 10 is shown. The AGIS 10 comprises a guide member 12, a control handle 14, and a signal processing unit 16. A transducer 17 is located at a distal end 18 of the guide member 12. The transducer 17 is operatively connected to the signal processing unit 16 by a cable 20 extending from the control handle 14 to the processing unit 16. As the transducer 17 detects air movement in a ventilating patient, it generates a raw electronic signal based thereon and relays that raw signal to the processing unit 16. The processing unit 16 then produces an amplified output signal (based on the raw signal) which may be used as an audio cue by the intubator to accurately indicate the distal end 18 position relative to a trachea 60 as shown in FIG. 2. Once in place, an endotracheal tube 44 can be slid over the guide member 12 and the guide member removed. While the first preferred embodiment permits guidance within the airway based on acoustic signals, catheters that detect other naturally occurring energy sources (i.e., energy sources that are not produced by an external medical device but rather by the patient's body itself) are also contemplated.

Having provided this brief overview, attention will now be focused on the components of the AGIS 10 as shown in FIGS. 1 and 2. The guide member 12 is a long, generally cylindrical tubular member approximately 24–26 inches (60–65 cm) long and 0.10–0.16 inches (3–4 mm) in diameter although other lengths and diameters are also contemplated within the scope of the invention. As shown in FIG. 2, the guide member distal end 18 is designed to be inserted into the mouth (or, optionally, through the nose) of the patient to be intubated. The guide member also includes a proximal end 22 located adjacent to the control handle 14. An intermediate section 24 extends between the ends 18 and 22.

The guide member may be flexible to improve its maneuverability within the patient's airway. In the first preferred embodiment, for example, the guide member 12 is made of a flexible material and includes an internal angulation wire 26. The angulation wire permits the intubator to angle the distal end 18 relative to the intermediate section 24 to better guide the end 18 through the airway. The manufacture and operation of such angulation mechanisms is well know in the art and is therefore not described in detail herein. The control handle 14 is designed to fit comfortably in the hand of the doctor or technician. A lever 28 or other device located on the control handle 14 is operatively connected to the angulation wire 26 such that the operator may comfortably manipulate the distal end 18 with a finger or thumb. In the first preferred embodiment, the angulation wire permits relative angulation between the intermediate section and the distal end of at least 80 deg in a first plane. The AGIS 10 itself may be rotated to provide relative angulation out of plane.

The guide member 12 may optionally be made of a malleable material that can be formed into the desired shape. Or, alternatively, it may be rigid or semi-rigid. Thus, various guide member constructions are contemplated.

Still referring to FIG. 1, one or more channels 30 is also provided. The channel 30 extends from the distal end 18 to the proximal end 22. A mating channel (not shown) in the handle 14 permits fluid communication between the channel 30 and an external connector 32 mounted to the handle 14. The connector 32 may be a standard luer lock adaptor. The purpose of the channel 30 and luer lock 32 is to permit the administration of local anesthetic to the airway. The channel may also be used to administer oxygen or "jet" ventilation if necessary. Those skilled in the art will realize that the channel 30 can be used for various other purposes not enumerated herein. The size of the channel is limited only by the size of the guide member 12. In the first preferred embodiment, the channel 30 has a 12 gage internal diameter.

Measuring indicia 34 may be included on the outer diameter of the guide member 12. The indicia 34 indicate the approximate insertion depth of the distal end 18 as shown in FIG. 2.

Having described the structure of the AGIS 10, attention will now be focused on its signal detection features. In the first preferred embodiment, the transducer 17 comprises an acoustic microphone located at the distal end 18 of the guide member 12. The microphone 17 detects the audible sounds created by air movement in the airway and generates the raw sound signal based thereon. The microphone 17 is connected by a wire (not shown) running through the guide member to the control handle 14. The handle 14 may have a connection jack (not shown) or, alternatively, a separate or integral cable 20. The cable 20 includes a connector 36 that connects to an input jack 38 located on the processing device 16.

The microphone 17 is designed to operate in adverse environments. Particularly, it can operate when exposed to or submerged within bodily fluids. Thus, it is immune to the effects of blood, mucous and saliva as may be encountered during intubation. Furthermore, the microphone 17 (and the remainder of the guide member 12) is bio-compatible.

Working in conjunction with the microphone 17 is the sound processing device 16. The sound processing device 16 provides power to and receives the raw sound signal from the microphone. The device 16 processes the raw signal and produces an amplified output signal. The sound processing device 16 may optionally include circuitry to filter out some portion of the raw signal, such as noise or, alternatively, it may merely amplify the raw signal.

The amplified output signal is transmitted through a speaker 40. In the first preferred embodiment, the speaker 40 is incorporated into the processing device 16. The device 16 may include a volume control 42 for volume adjustment relative to ambient. The device 16 is lightweight and portable such that it may comfortably be attached to the intubator's shirt or alternatively, sit near the patient.

While the speaker is described herein as integral to the device 16, it is also contemplated that it may comprise an earphone or headset (not shown) that plugs into a headset jack (also not shown) on the device 16. Alternatively, a conventional wireless connection (e.g., radio frequency) could be established between the device 16 and the speaker/headphones 40. Optionally, the wireless connection could be established between the microphone itself and the speaker/headphones. Thus, the connection between the microphone and the speaker can be by any conventional method.

The device 16 may be adapted to receive power from a multitude of sources including but not limited to 120V/240V AC. Because the AGIS 10 is portable, it may also be powered by batteries. Other power sources commonly available are also contemplated to be within the scope of the invention.

Having described the first preferred embodiment of the AGIS 10 in detail, attention will now be focused on FIG. 2 and a first preferred method of use. In the elective situation, the patient may be sedated and topical and nerve block anesthesia may be administered through conventional methods. A lubricated endotracheal tube 44 may be first placed over the guide member 12. The guide member may then be inserted through the nose or mouth 68 of the spontaneously breathing patient or through a laryngeal mask airway (LMA). As the distal end 18 is advanced beyond the anesthetized area, additional topical anesthesia may be administered through the channel 30 by attaching a syringe (or other administering device) to the luer lock 32. Alternatively, oxygen may be administered through the channel.

As the stylet is advanced, the microphone 17 at the distal end 18 of the guide member 12 detects the audible sounds produced by air movement within the airway and produces the raw sound signal. The processing device 16 receives and amplifies the raw sound signal and generates the amplified sound output signal. The amplified signal is transmitted through the speaker 40. The amplified signal may then be used as audio cues to guide the distal end 18 within the airway. The audio cues will intensify as the distal end 18 approaches the glottis 65 as the airway is more narrow here and the corresponding air flow is more rapid and turbulent. The intubator may direct the guide member with gentle force and manipulation of the lever 28 to angulate the distal end. The patient may be asked to phonate (e.g., say "e") to better assist the intubator in directing the AGIS 10. If the end 18 is advanced past the epiglottis 62 posteriorly into the esophagus 66, the audio cues may become muffled or even disappear. When the distal end 18 is just above the glottis 65 in the vallecula or to either side of the glottis 65 in a pyriform sinus, there will also be dampening of the audio cues and resistance to advancement of the guide member. When the stylet passes the vocal cords 64, there will be a change in the quality of the audio cue, loss of vocalization, and possibly a cough.

Where the airway has contracted to a point where it will not accommodate the endotracheal tube 44 (e.g., as may occur in the presence of trauma, edema, or tumor), the AGIS 10 permits the administering of jet ventilation via the channel 30 to temporarily ventilate and oxygenate the patient. Otherwise, once the distal end 18 is correctly placed (i.e., has passed the vocal cords), the endotracheal tube 44 may be advanced over the guide member 18 and the AGIS 10 may be removed. Confirmation of proper placement can be made by the usual methods including chest auscultation and carbon dioxide detection.

Figure 3:
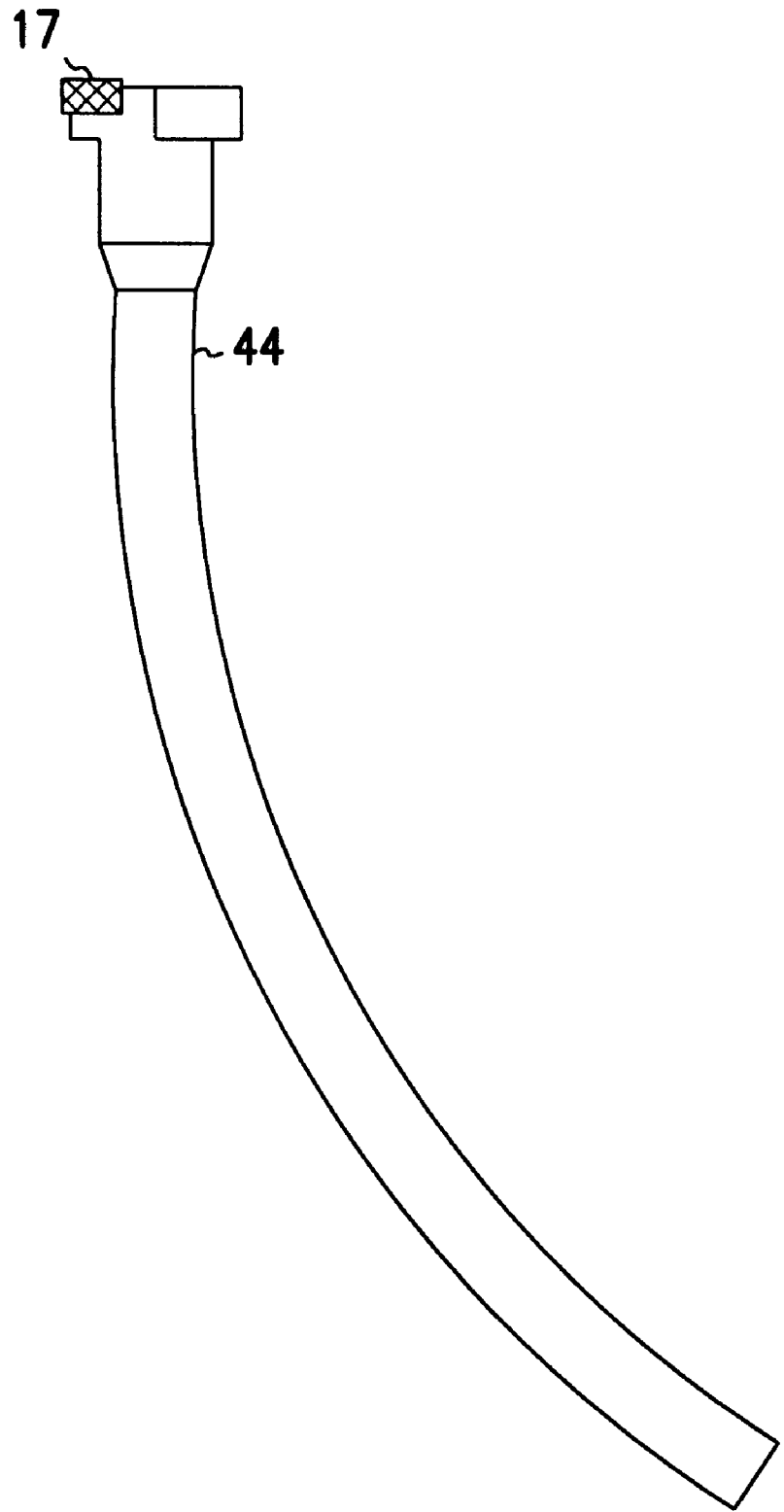
FIG. 3 is a side view of another embodiment of the present invention wherein a microphone is attached directly to an endotracheal tube.

In a second preferred embodiment shown generally in FIG. 3, a microphone 17 is attached directly to an endotracheal tube 44 wherein the tube can be inserted without the use of a stylet. The microphone may be attached to the proximal end of the tube to detect sound waves that propagate through the tube.

While the invention has been described with reference to the first and second preferred embodiments, other embodiments and variations are also contemplated to fall within the scope of the invention. For example, the microphone may be directional such that it is more sensitive to forward sounds than peripheral sounds. Alternatively, more than one microphone may be provided to sense both peripheral and forward sounds. In yet another variation, the guide member 12 may be hollow (i.e., no angulation wire 26 or channel 30) to accommodate a larger, higher quality microphone.

In yet another preferred embodiment, the transducer 17 may take advantage of the Doppler effect to detect air movement in the airway. Specifically, the Doppler effect transducer may detect a change in the observed frequency of an emitted acoustic wave (or other energy wave) resulting from the relative motion of the transducer within the airway.

While described herein with reference to sound detection technology, it is also contemplated that other detection technologies that produce a signal in response to a naturally occurring energy source may be employed. For example, a pressure transducer that measures changes in pressure within the airway as the patient exhales may be used. Still other modifications can be made to the preferred embodiments and still fall within the scope of the invention.

The use of AGIS provides another less traumatic technique having safety characteristics similar to that of fiberoptics. By taking advantage of the acoustic characteristics of air movement through the upper airway of a breathing patient rather than the visual appearance of the glottis, AGIS will work in some situations where fiberoptic techniques fail (e.g., in the presence of blood, vomitus or secretions in the airway). Furthermore, it needs no bulky, external energy (e.g., light or sound) source. Accordingly, the sound processing device may be a lightweight, portable unit that is convenient to carry. While it can be used as a backup device to fiberoptics, it may also be chosen as the instrument of choice in the OR, ER, or ICU. As it requires less expertise and skill than fiberoptic techniques, it may also be appropriate for use by field paramedics, an advantage not realized with fiberoptics. Finally, as compared to fiberoptic scopes, AGIS is less expensive, potentially more durable, and less bulky as no light source or heavy electronic equipment is required.

Preferred embodiments of the present invention are described above. Those skilled in the art will recognize that many embodiments are possible within the scope of the invention. Variations and modifications of the various parts and assemblies can certainly be made and still fall within the scope of the invention. Thus, the invention is limited only by the following claims, and equivalents thereto.

I claim:

1. A method for intubating a breathing patient, the method comprising:

inserting an endotracheal tube over an intubating stylet guide member wherein the guide member has a distal end;

inserting the distal end into an airway of the patient wherein the distal end includes a microphone;

detecting audible sounds at the microphone caused by air passing through the airway;

generating a raw signal based on the detected audible sounds;

receiving and processing the raw signal with a sound processing device; and generating an output signal based on the raw signal and transmitting the output signal through a sound output device.

2. The method of claim 1 further comprising the step of amplifying the output signal.

3. The method of claim 2 further including the step of using the output signal as an audio cue to assist in positioning the distal end.

4. The method of claim 3 further comprising the step of manipulating an angulation wire within the guide member to position the distal end.

5. The method of claim 4 further comprising the step of delivering a medicinal fluid through a channel within the guide member.

6. The method of claim 5 further comprising the step of removing the guide member once the endotracheal tube is properly positioned, leaving the endotracheal tube in place.

* * * * *